United States Patent [19]
Johnson et al.

[11] Patent Number: 5,626,133
[45] Date of Patent: May 6, 1997

[54] GESTATIONAL COMPUTER

[76] Inventors: Mary A. Johnson, 706 Greenview Ave., Des Plaines, Ill. 60016; Erwin G. Szela, Jr., 211 E. Forest, Palatine, Ill. 60067

[21] Appl. No.: 514,067
[22] Filed: Aug. 11, 1995
[51] Int. Cl.$^6$ .................................................. A61B 8/00
[52] U.S. Cl. ..................... 128/630; 128/660.01; 128/738
[58] Field of Search .................... 128/630, 660.01, 128/660.02, 661.03, 660.07, 661.07, 738, 774; 364/413.01, 413.02, 413.12, 413.25

[56] References Cited

U.S. PATENT DOCUMENTS

| | | | |
|---|---|---|---|
| 4,005,571 | 2/1977 | Wolff | 58/39.5 |
| 4,443,851 | 4/1984 | Lin | 364/413.12 |
| 4,465,077 | 8/1984 | Schneider | 364/413.12 |
| 4,493,043 | 1/1985 | Forbath | 364/569 |
| 4,527,906 | 7/1985 | Jezbera | 368/107 |
| 5,031,161 | 7/1991 | Kendrick | 368/280 |
| 5,327,403 | 7/1994 | Bond | 368/107 |
| 5,450,857 | 9/1995 | Garfield et al. | 128/774 X |
| 5,492,940 | 8/1995 | Secker et al. | 128/661.07 |

FOREIGN PATENT DOCUMENTS 2617618  1/1989  France.

*Primary Examiner*—Francis Jaworski
*Attorney, Agent, or Firm*—Arnold, White & Durkee

[57] ABSTRACT

A hand-held gestational computer comprises a microprocessor programmed to receive input signals representing the current date and at least one parameter is selected from the group consisting of the date of the first day of the last menstrual period, estimated gestation age, conception date, estimated date of confinement by ultrasound analysis, and estimated fetal weight. The microprocessor produces output signals representing the value of at least one parameter selected from the group consisting of estimated gestation age, estimated date of confinement, conception date, estimated fetal weight, and the percentile of the estimated fetal weight for the estimated gestation age. There is a palm-sized housing for the microprocessor, a display and one or more pushbuttons for sequentially selecting different display fields in which data is to be entered, and sequentially displaying data available for entry in the selected display field.

10 Claims, 18 Drawing Sheets

GESTATIONAL COMPUTER

FIELD OF THE INVENTION

This invention relates to hand-held gestational computers for use by physicians specializing in the field of obstetrics or gynecology. In addition, any person interested in gestational calculations for the gestational cycle of any organism may use this invention, including other physicians, nurses, ultrasonographers, other medical personnel, patients, veterinarians or biological researchers.

SUMMARY OF THE INVENTION

It is a primary object of the present invention to provide an improved hand-held electronic gestational computer which facilitates use of the computer with one hand.

It is another object of this invention to provide an improved hand-held electronic gestational computer which automatically displays the more accurate of the estimated dates of confinement determined by computation and by ultrasound analysis.

A further object of this invention is to provide an improved hand-held electronic gestational computer which automatically determines and displays the estimated fetal weight as of the current date, or the percentile for a manually entered fetal weight as of a selected date.

Still another object of this invention is to provide an improved hand-held electronic gestational computer which can be efficiently and economically manufactured.

Other objects and advantages of the invention will be apparent from the following detailed description in the accompanying drawings.

In accordance with the present invention, the foregoing objectives are realized by providing a hand-held gestational computer which includes a microprocessor programmed to receive input signals representing the current date and at least one parameter selected from the group consisting of the date of the first day of the last menstrual period, estimated gestation age, conception date, estimated date of confinement by ultrasound analysis, and estimated fetal weight, and to produce output signals representing the value of at least one parameter selected from the group consisting of estimated gestation age, estimated date of confinement, conception date, estimated fetal weight, and the percentile of the estimated fetal weight for the estimated gestation age. The microprocessor is contained in a palm-sized housing which includes a display device responsive to the output signals from the microprocessor for producing displays of the parameter values represented by the output signals. Multiple manually operable actuators are connected to the microprocessor for sequentially selecting different fields in which data is to be entered, sequentially displaying data available for entry into the selected field and entering selected data in selected fields.

In one preferred embodiment of the invention, the memory associated with the microprocessor stores data representing the 50-percentile fetal weight for each of a range of different gestation ages, and the microprocessor is programmed to retrieve and display the 50-percentile fetal weight corresponding to the displayed estimated gestation age. The memory optionally contains data representing the percentile number for each of a range of different combinations of fetal weight and gestation age, and the microprocessor is programmed to retrieve and display the percentile number corresponding to the displayed estimated fetal weight and estimated gestation age.

In another preferred embodiment, the memory associated with the microprocessor stores data indicating whether the computed estimated date of confinement or the estimated date of confinement estimated from ultrasound analysis, is preferred over certain ranges of estimate gestational ages. The microprocessor is programmed to calculate and display the gestational values using the preferred estimated date of confinement. The microprocessor optionally includes a separate display of the date of the ultrasound analysis.

BRIEF DESCRIPTION OF THE DRAWINGS

FIG. 3b is a sectional view taken diametrically through the computer of FIG. 3a;

FIG. 4b is a sectional view taken diametrically through the computer of FIG. 4a;

DETAILED DESCRIPTION OF THE PREFERRED EMBODIMENTS

Figure 1:
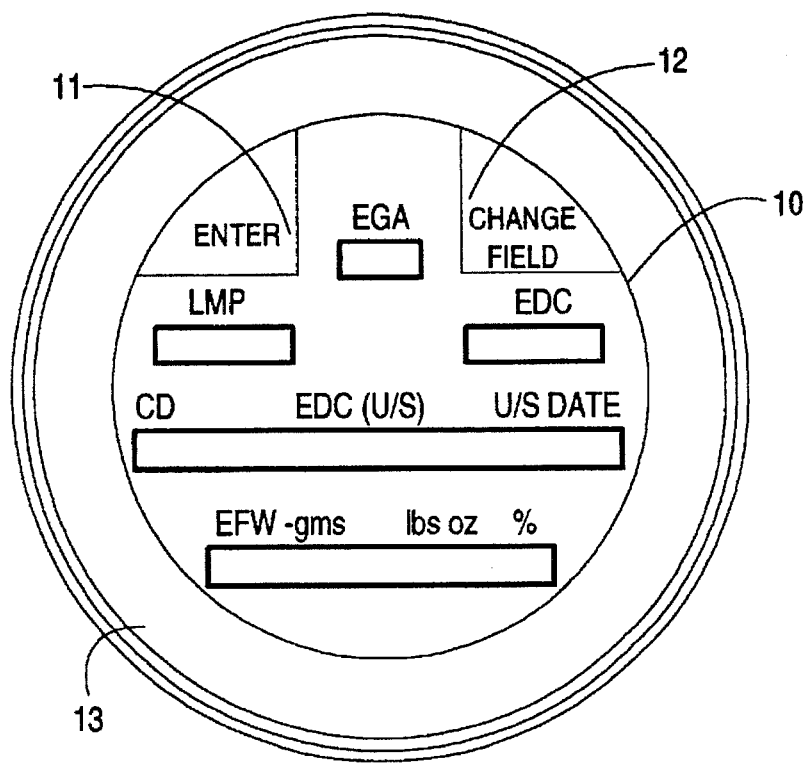
FIG. 1 is a plan view of the front of a gestational computer embodying the present invention.

While the invention is susceptible to various modifications and alternative forms, specific embodiments thereof have been shown by way of example in the drawings and will be described in detail. It should be understood, however, that it is not intended to limit the invention to the particular forms disclosed, but on the contrary, the intention is to cover all modifications, equivalents, and alternatives tailing with the spirit and scope of the invention as defined by the appended claims.

Turning now to the drawings, FIG. 1 shows the face of a gestational computer in a palm-sized plastic housing 10. The face of the housing 10 contains openings for five different liquid crystal displays having fields for displaying the following parameters:

EGA—estimated gestational age in weeks and days.

LMP—last menstrual period (the date of the first day of a woman's last menstrual period) in terms of month and day.

EDC—estimated date of confinement (due date) in weeks and days.

CD—conception date in terms of month and day.

EDC (U/S)—estimated date of confinement based on ultrasound data in weeks and days.

U/S Date—date of ultrasound analysis in terms of month and flay.

EFW—estimated fetal weight in grams and pounds and ounces.

%—percentile of the estimated fetal weight.

To permit the manual entry of data into the computer, a pair of manually operated buttons 11 and 12 are mounted near each other along the edge of the face of the housing 10. The button 11 is an "enter" button 11, and the button 12 is a "change field" button. The first time either the "enter" button 11 or the "change field" button 12 is pressed, the microprocessor initiates blinking of one of the fields in which data is to be entered. The blinking field also displays an initialized value for that particular field. While the field is blinking, the user can scroll through a range of values for that particular field, until the desired value is reached. At that point the "enter" button 11 is pressed to enter the selected value, and the microprocessor then stores and displays the selected value. Blinking of the active field continues until the "enter" button 11 is pressed to enter the selected value, or the "change field" button 12 is pressed to move to the next field, or a fixed time period expires.

Figure 5:
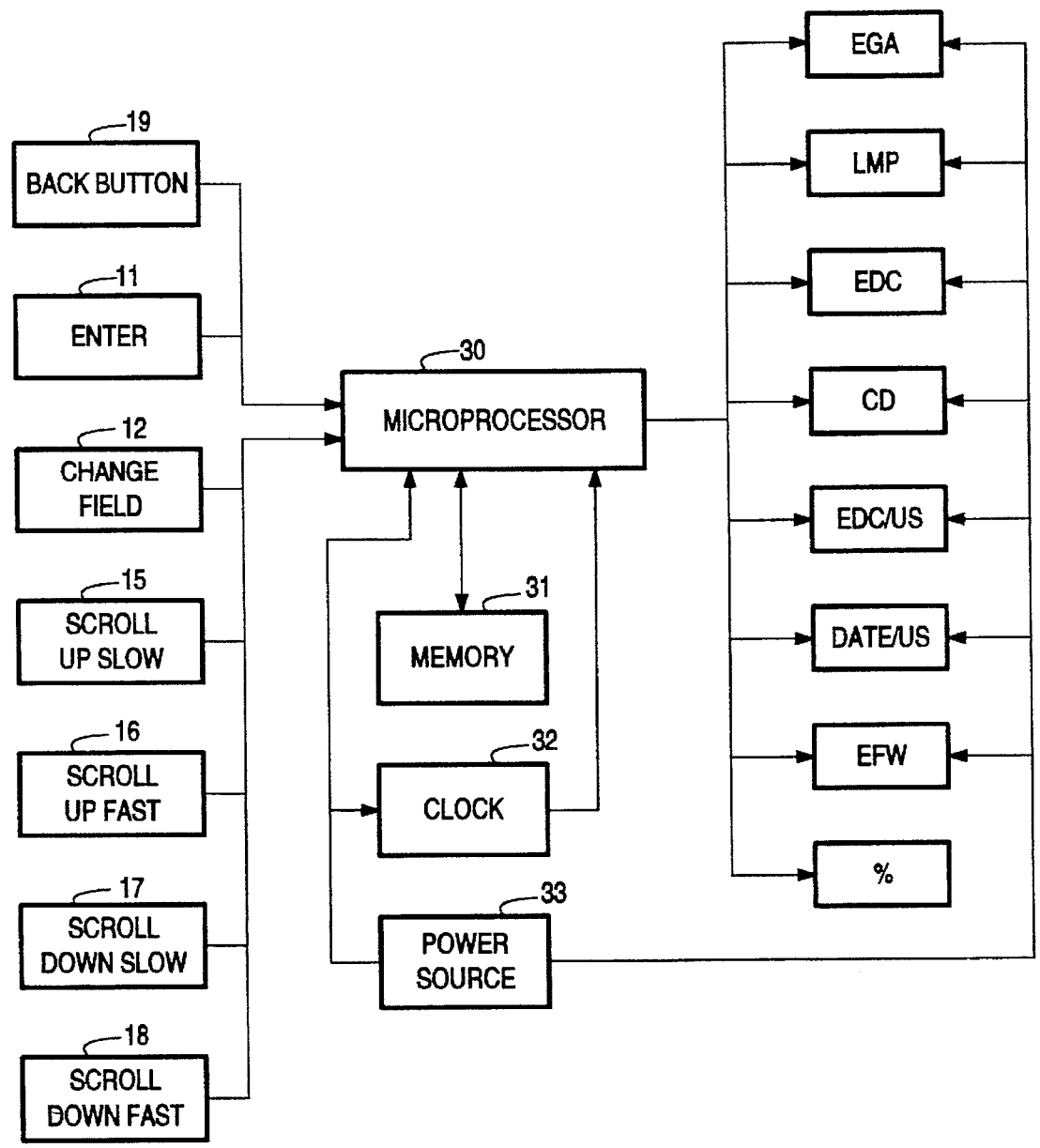
FIG. 5 is a block diagram of the electronic system in the gestational computer of FIG. 1.

Scrolling is effected by turning an annulus 13 that is rotatably mounted in an annular recess 14 formed by the housing 10 around the periphery of the raised face of the housing. Turning the annulus 13 clockwise to a first position causes the value in the active field to increase at a relatively slow rate. To accelerate the rate at which the displayed value increases, the annulus 13 is turned clockwise to a second position. Turning the annulus 13 in the counterclockwise direction causes the displayed value to decrease at either a slow or fast rate, depending on how far the annulus is turned. Turning the annulus to these different positions actuates different switching devices inside the housing, so that the microprocessor 30 (described below) that controls the scrolling rate receives one of four scrolling signals: a "slow increasing scroll" signal 15, a "fast increasing scroll" signal 16, a "slow decreasing scroll" signal 17, or a "fast decreasing scroll" signal 18 (FIG. 5). No matter which of the four scrolling signals is selected by the user, the microprocessor will complete all of the steps on the flow charts described below. However, the rate and direction of the scrolling display changes depend upon which mode is selected. To terminate scrolling, the annulus 13 is returned to its neutral starting position.

If the blinking of a given field continues for a selected time period, such as 30 seconds, without any button being pressed, the microprocessor 30 automatically goes into a sleep mode. In this mode the microprocessor terminates power to the display fields, causing them to fade to empty. The microprocessor will remain in the sleep mode until either the "enter" button 11 or the "change field" button 12 is pressed again. After either button is pressed, the last active display field will resume blinking.

The back of the housing 10 contains an on-off switch (not shown) and a back button 19 (FIG. 5) for reinitializing certain values. The first time the unit is operated, the display prompts the user to enter the current date and time and a desired LMP offset value, as described in more detail below. These values may be subsequently reinitalized by manually actuating the back button 19. Whenever the back button 19 is depressed, the display prompts the user to enter the current date and time and desired LMP offset value. The entered values are then permanently stored by the microprocessor 30, which automatically updates the date and time at frequent intervals.

Figure 2:
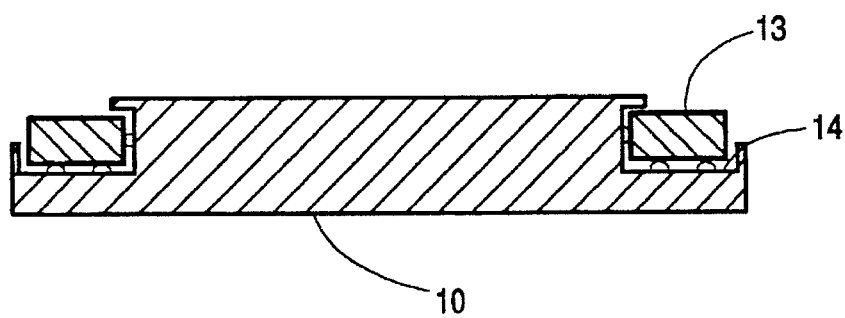
FIG. 2 is a sectional view taken diametrically through the computer of FIG. 1.
Figure 3A:
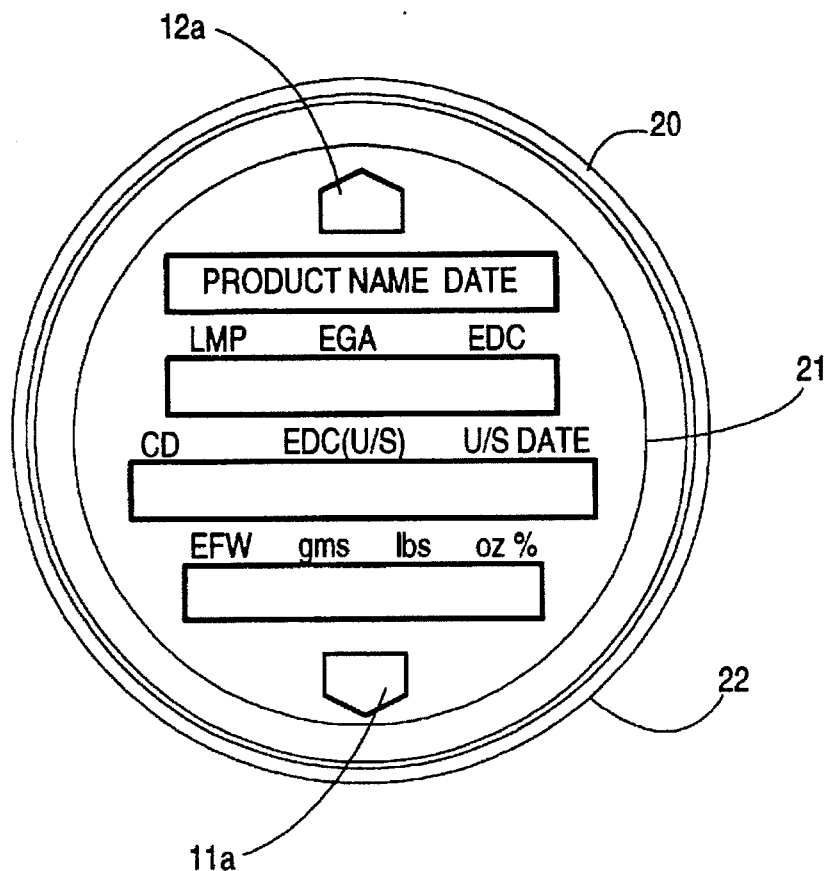
FIG. 3a is a plan view of a modified gestational computer embodying the present invention.
Figure 3B:
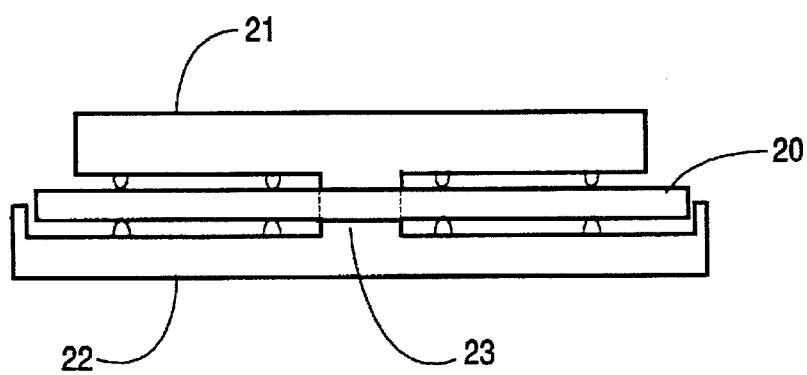

The computer of FIGS. 1 and 2 preferably has a size that permits it to be easily held and operated with one hand. For example, the computer may have a diameter of about three inches and a thickness of about a quarter inch. The buttons 11 and 12 are located near the periphery of the device so that they can be easily pressed with the fingers of the same hand that is used to hold the computer. The annulus 13 can also be turned with the same finger or fingers used to press the buttons 11 and 12. The rotational movement of the annulus 13 is a manipulation familiar to physicians who are accustomed to using the conventional printed mechanical "gestational wheels" that have been used for many years to correlate LMP and conception dates with average fetal weight and length, and to estimate confinement dates.

FIGS. 3a,3b and 4a,4b illustrate alternative constructions of the hand-held gestational computer. In the embodiment shown in FIGS. 3a and 3b the "enter" button 11 and the "change field" button 12 are located at diametrically opposed positions along the periphery of the raised face of a housing 20. For the scrolling functions, a thin rotatable wheel 21 is sandwiched between the housing 21 and a case 22. The thin wheel 20 is rotatably mounted on a central post 23 which connects the housing 21 to the case 22. The wheel 20 rotates within the cavity formed by the case 22 and the housing 21.

Figure 4A:
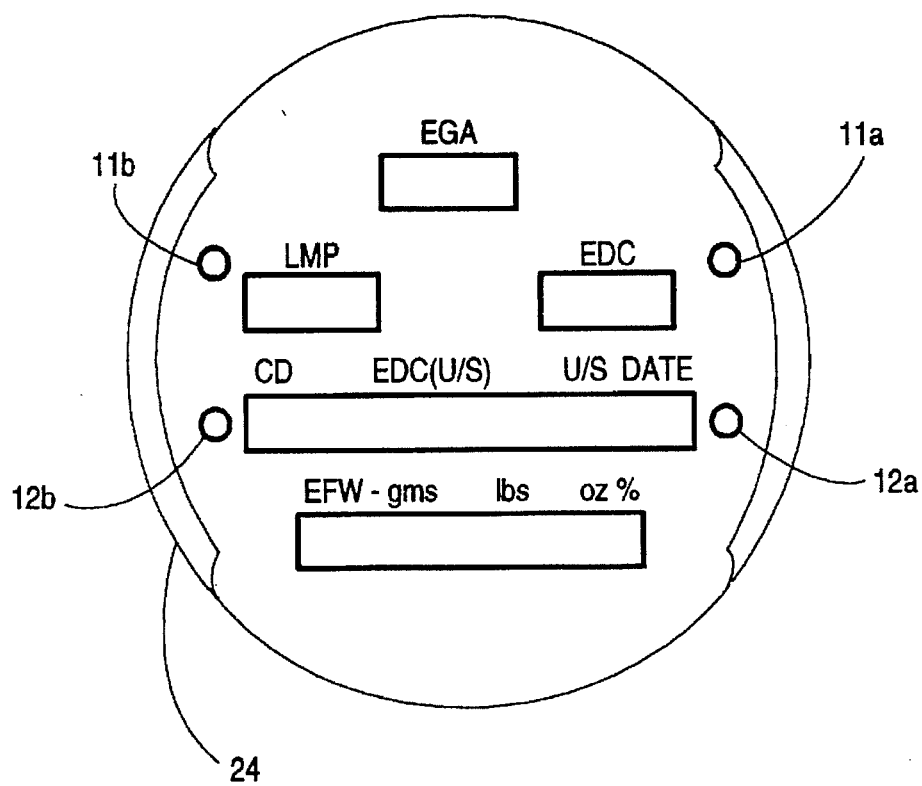
FIG. 4a is a plan view of a modified gestational computer embodying the present invention.
Figure 4B:
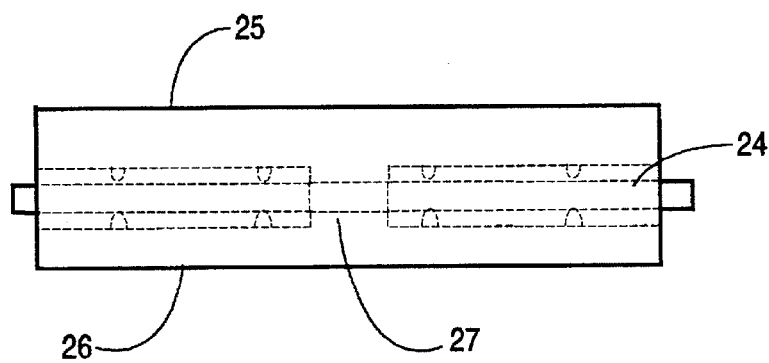

The embodiment of FIGS. 4a and 4b includes two pairs of "enter" and "change field" buttons 11a, 12a and 11b, 12b. The buttons in each pair are mounted near each other along the edge of the face of the housing opposing the other pair of buttons. The placement of the two pairs of buttons 11a, 12a and 11b,12b enables both right and left handed users to easily use the unit with one hand. A scrolling wheel 24 is sandwiched between a housing 25 and a case 26. The wheel 24 is rotatably mounted to a central post 27 which connects the housing 25 to the case 26. Opposite side portions of the housing 25 and case 26 are cut out to expose diametrically opposite portions of the wheel 24 to facilitate engagement of the wheel 24 by the user.

The gestational computer display may be composed of any number of fields to display a variety of gestational values and information. The examples shown are not intended to cover all of the possible display fields.

The gestational computer may also be modified to include an adapter that permits it to be attached to other medical equipment such as hand-held dopplers, ultrasound equipment and NST machines. Examples of such adapters are snaps, suction cups or magnets affixed to the case to allow easy attachment to other such products.

Referring now to FIG. 5, there is shown an upper level block diagram of an illustrative microprocessor-based control system for receiving input signals from the manually operated buttons and annulus, and controlling the various fields on the face of the computer. This control system includes a microprocessor 30 which accepts input signals from the "enter" button 11, the "change field" button 12, and the back button 19, as well as the four scrolling signals controlled by the position of the annulus 13. The microprocessor 30 is connected to a memory 31, a clock 32 and a power source (e.g., a battery) 33. The microprocessor 30 produces output signals to control the multiple fields discussed above, all of which are powered by the same power source 33 which powers the microprocessor.

Referring next to FIGS. 6–15, there is shown a series of flow charts illustrating the sequence of operations involved in the operation of the microprocessor 30 in response to the various input signals, for controlling the various fields on the front of the computer housing.

Figure 6A:
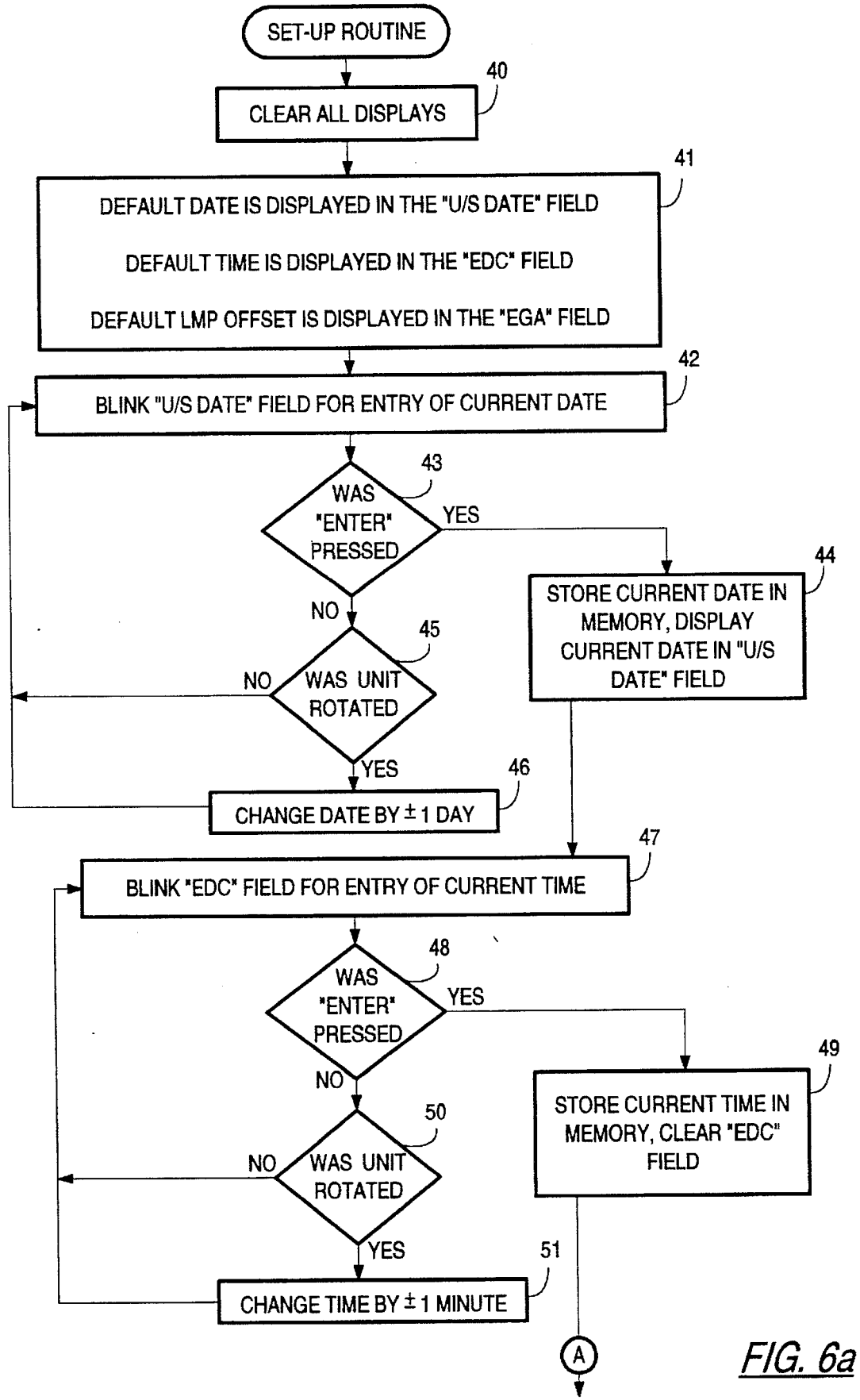
FIG. 6 is a flow chart of the set-up routine for initializing the microprocessor in the electronic system of FIG. 5.
Figure 6B:
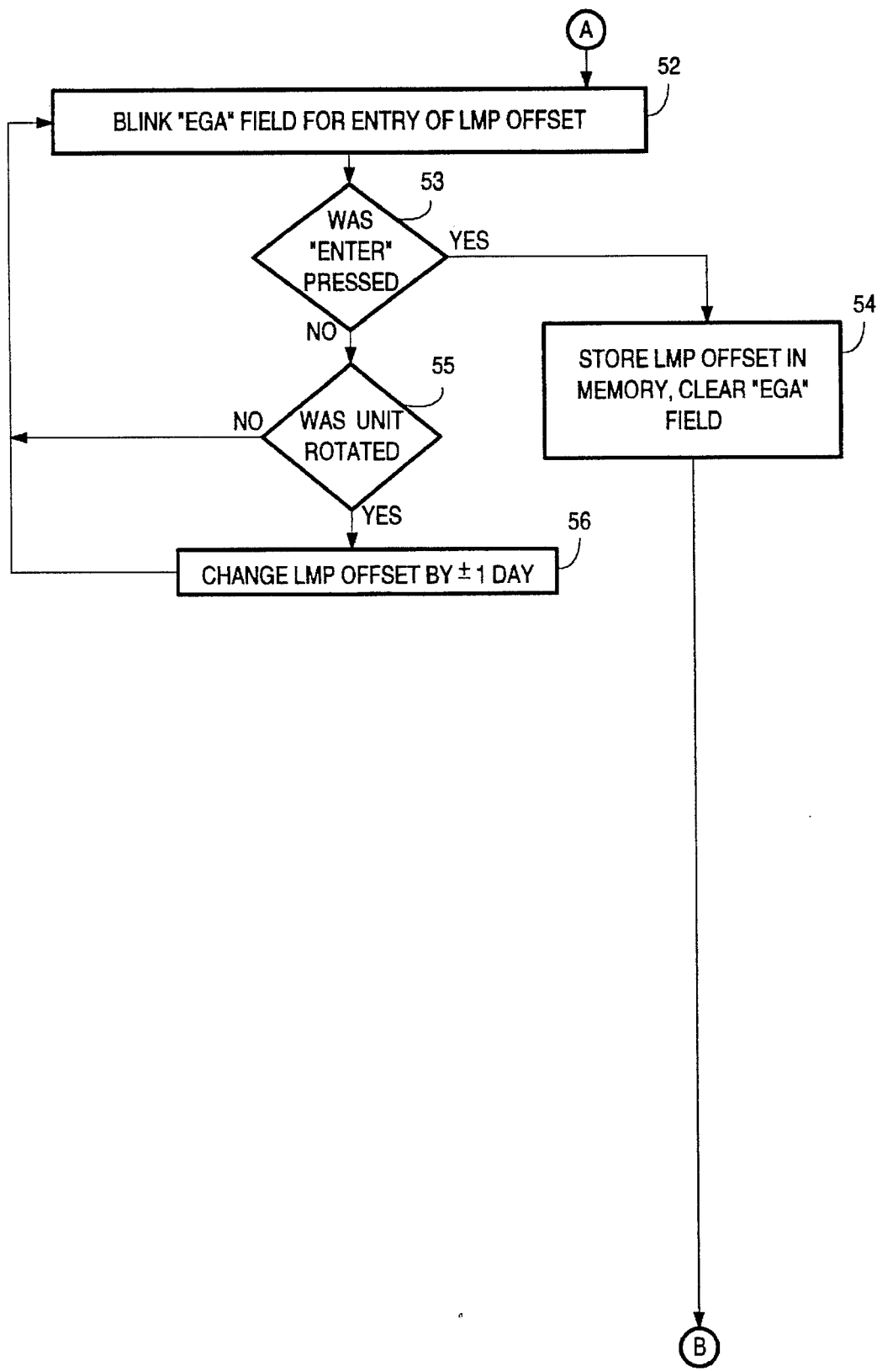

FIG. 6 is a flow chart for the set up routine of the microprocessor program. The first time the user operates the unit, the user must go through the set up routine. After completing the set up procedures, the computer will not execute this set up routine again unless the user presses the back button 19. When the unit is used for the first time, or when the back button 19 is pressed, the set up routine begins by clearing all fields at step 40. The user is then prompted to enter the current date, time and LMP offset, and the computer displays a default date in the "U/S Date" field, a default time in the "EDC" field, and a default LMP offset in the "EGA" field at step 41.

For entry of the correct current date, the "U/S Date" field containing the default date is blinked at step 42. If the user has pressed the "enter" button 11 to accept the displayed date as the current date, step 43 yields an affirmative answer which causes the computer to store that date in the memory as the current date and to temporarily display that date in the "U/S Date" field at step 44.

Whenever step 43 produces a negative answer, the system proceeds to step 45 to determine whether the annulus 13 has been turned to initiate scrolling of the displayed date. If the answer is negative, the system returns to step 42 to continue the blinking of the field. An affirmative answer at step 45 results in a one-day change in the displayed date at step 46 before returning to step 42. The date displayed will continue to blink, and the date will continue to change, as long as the annulus 13 remains in a scroll position. When the correct current date appears on the screen, the user must press the "enter" button 11 to accept the displayed date as the current date at steps 43 and 44.

Once the correct current date has been accepted and stored at step 44, the user is prompted to enter the current time. At step 47, the "EDC" field containing the default time is blinked for entry of the current time. If the user has pressed the "enter" button 11 to accept the displayed time as the current time, step 48 yields an affirmative answer which causes the computer to store that time in the memory as the current time and to clear the "EDC" field at step 49.

Whenever step 48 produces a negative answer, the system proceeds to step 50 to determine whether the annulus 13 has been turned to initiate scrolling of the displayed time. If the answer is negative, the system returns to step 47 to continue the blinking of the field. An affirmative answer at step 50 results in a one-minute change in the displayed time at step 51 before returning to step 47. The time displayed will continue to blink, and the time will continue to change, as long as the annulus 13 remains in a scroll position. When the correct current time appears on the screen, the user must press the "enter" button 11 to accept the displayed time as the current time at steps 48 and 49.

Once the current time has been accepted and stored at step 49, the user is prompted to enter the LMP offset. At step 52, the "EGA" field containing the default LMP offset is blinked for entry of the correct LMP offset. If the user has pressed the enter button to accept the displayed date as the LMP offset, step 53 yields an affirmative answer which causes the computer to store that LMP offset in the memory as the correct LMP offset and to clear the "EGA" field at step 54.

Whenever step 53 produces a negative answer, the system proceeds to step 55 to determine whether the annulus 13 has been turned to initiate scrolling of the displayed LMP offset. If the answer is negative, the system returns to step 52 to continue the blinking of the field. An affirmative answer at step 55 results in a oneday change in the displayed LMP offset at step 56 before returning to step 52. The LMP offset displayed will continue to blink, and the LMP offset will continue to change, as long as the annulus 13 remains in a scroll position. When the correct LMP offset appears on the screen, the user must press the "enter" button 11 to accept the displayed LMP offset as the correct LMP offset at steps 53 and 54.

Figure 7:
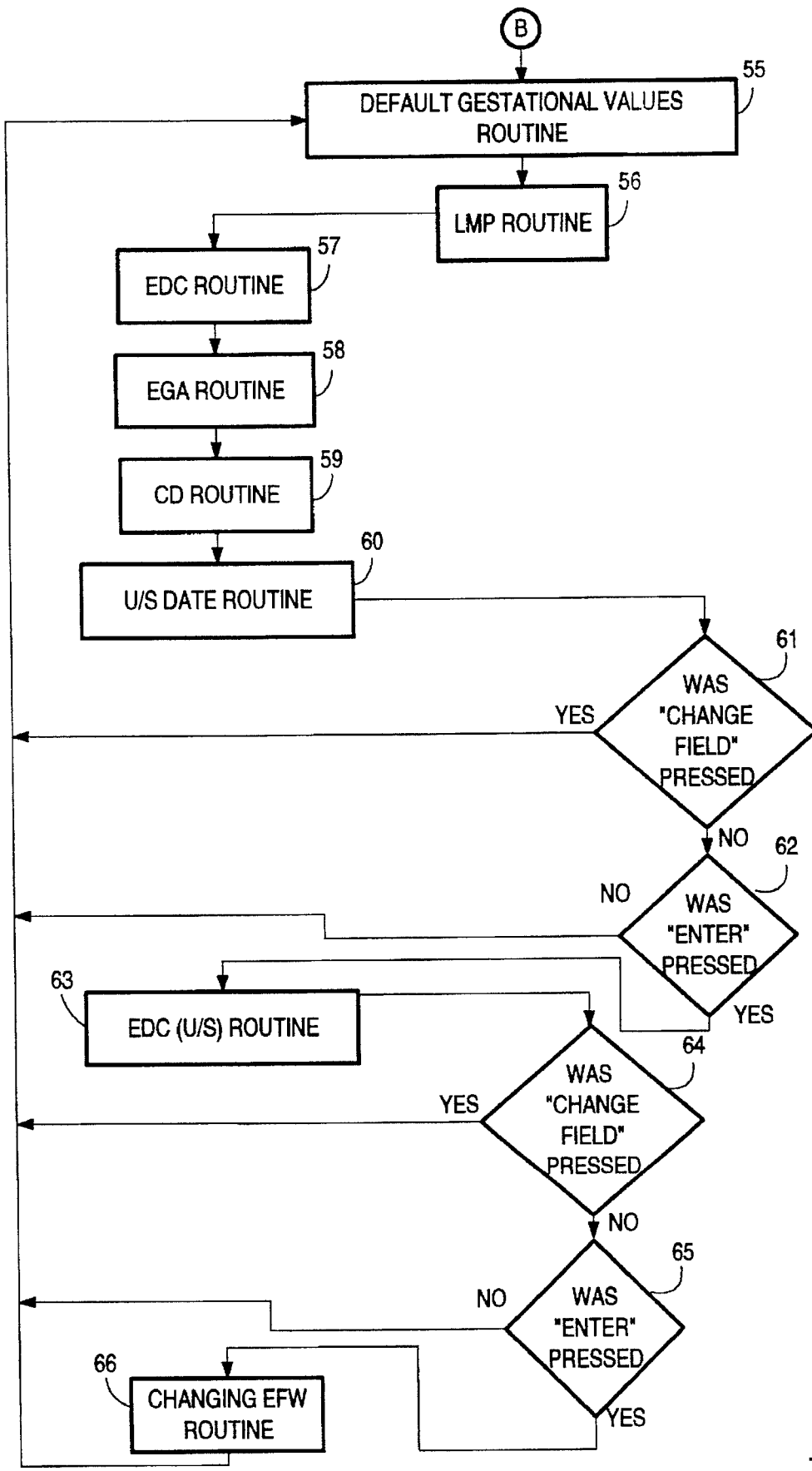
FIG. 7 is a flow chart of the main program for controlling the microprocessor in the electronic system of FIG. 5.

After the set up procedures have been completed, the computer moves to the main program shown in a flow chart of FIG. 7. The flow chart shows the routines which will prompt the user to enter gestational values for calculations. Each block is more fully explained below by additional flow charts.

Figure 8:
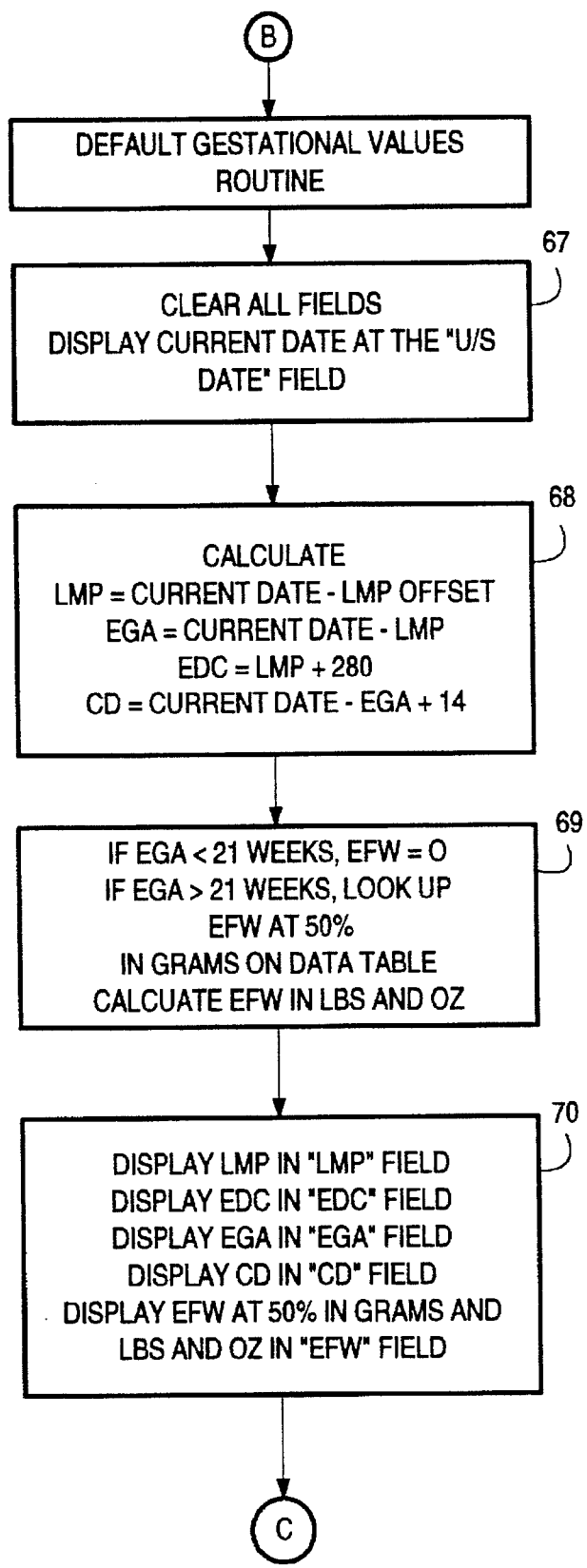
FIGS. 8 through 15 are flow charts of subroutines executed at various steps of the main program shown in FIG. 7.

FIG. 8 shows a flow chart for the default gestational values routine of step 55 in FIG. 7. Step 67 clears all fields and displays the current date at the "U/S Date" field. At step 68, the default gestational values are calculated with the following equations: LMP=(current date)−(LMP offset); EGA=(current date)−LMP; EDC=LMP+280; and CD=(current date)−EGA+14. Next at step 69, the 50-percentile value of EFW is obtained. If EGA is less than 21 weeks, then EFW is zero; however, if EGA is greater than 21 weeks, the EFW at 50% in grams is obtained from Table 1 using the EGA value. Once the EFW at 50% in grams is determined, the EFW at 50% in pounds and ounces is calculated. After the calculations have been completed, the computer displays the LMP in the "LMP" field, EDC in the "EDC" field, EGA in the "EGA" field, CD in the "CD" field, and the EFW at 50% in grams and in pounds/ounces in the "EFW" field at step 70.

Figure 9:
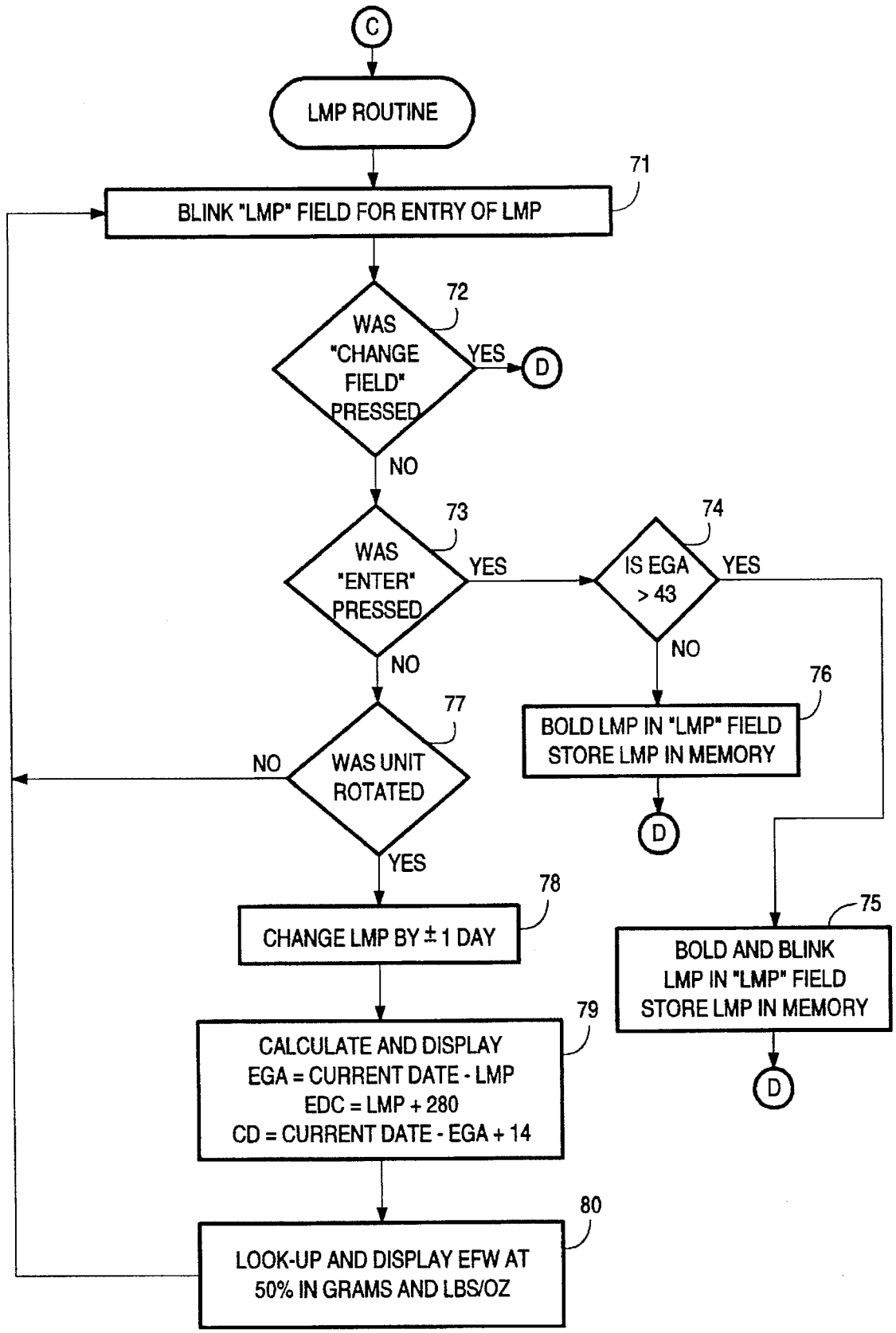

Once the default gestational values routine has been completed, the system advances to the LMP routine of step 56 in FIG. 7. FIG. 9 is a flow chart of the LMP routine. At step 71, the "LMP" field containing the default LMP is blinked to prompt the user to enter a LMP value. If the user does not wish to enter in a LMP value, the "change field" button 12 may be pressed to produce an affirmative answer at step 72. This causes the system to bypass the LMP routine and jump directly to the EDC routine of FIG. 10.

Step 73 determines whether the user has pressed the "enter" button 11 to accept the displayed LMP value. An affirmative answer at this step advances the system to step 74 which tests the entered LMP value. If the EGA value calculated from the entered LMP is greater than forty-three weeks, the user has entered erroneous data. An affirmative answer at step 74 stores the LMP in memory and bolds and blinks the LMP value in the "LMP" field at step 75 to indicate an erroneous LMP was entered. A negative answer at step 74 stores the LMP in memory and bolds the LMP value in the "LMP" field at step 76 to indicate an appropriate LMP was entered.

A negative answer at step 73 advances the system to step 77 which determines whether the user has turned the annulus 13 to initiate scrolling of the displayed LMP. An affirmative answer at step 77 changes the displayed LMP by one day at step 78. A negative response at step 77 returns the system to step 71.

Each time the LMP is changed by the user, the microprocessor updates the other gestational values by calculating EGA=(current date)−LMP; EDC5=LMP+280; and CD=(current date)−EGA+14, and displays these values in their appropriate fields at step 79. The 50-percentile value of EFW in grams and pounds/ounces is also updated and displayed at step 80 by executing the same steps described above for step 69. The system then returns to step 71 so that the "LMP" field will continue to blink the LMP value, allowing the user to continue scrolling until the desired LMP value appears on the field. The user then must press the "enter" button 11 to accept the displayed LMP at step 73.

Figure 10:
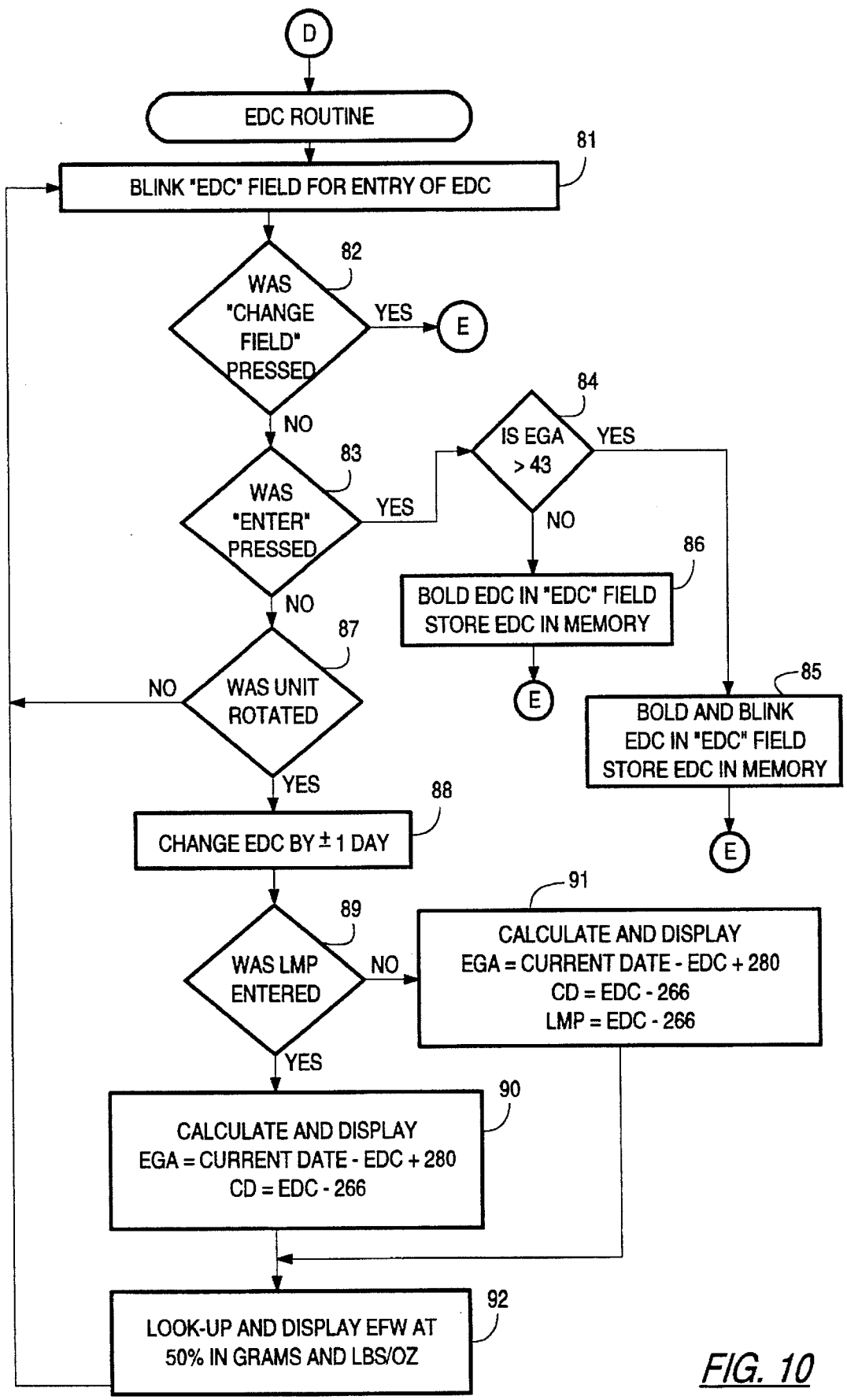

After the LMP value has been entered, the system advances to the EDC routine of step 57 in FIG. 7. FIG. 10 is a flow chart of the EDC routine. At step 81, the "EDC" field containing the default EDC is blinked to prompt the user to enter an EDC value. If the user does not wish to enter in a EDC value, the "change field" button 12 may be pressed to produce an affirmative answer at step 82. This causes the system to bypass the EDC routine and jump directly to the EGA routine in FIG. 11.

Step 83 determines whether the user has pressed the "enter" button 11 to accept the displayed EDC. An affirmative answer at this step advances the system to step 84 which tests the entered EDC value. If the EGA value calculated from the entered EDC is greater than forty-three weeks, the user has entered erroneous data. An affirmative answer at step 84 stores the EDC in memory and bolds and blinks the EDC value in the "EDC" field at step 85 to indicate an erroneous EDC was entered. A negative response at step 84 stores the EDC in memory and bolds the EDC value in the "EDC" field at step 86 to indicate an appropriate EDC was entered.

A negative answer at step 83 advances the system to step 87 which determines whether the user has turned the annulus 13 to initiate scrolling of the displayed EDC. An affirmative answer at step 87 changes the displayed EDC by one day at step 88. A negative response at step 87 returns the system to step 81.

Each time the EDC is changed by the user, the microprocessor updates the other gestational values. First, step 89 tests whether a LMP value was previously entered by the user. An affirmative answer at step 89 updates the CD and EGA gestational values by calculating EGA=(current date) −EDC+280; and CD= EDC −266, and displays these values in their appropriate fields at step 90. A negative response at step 89 updates the LMP, CD and EGA gestational values by calculating LMP=EDC 266; EGA=(current date)−ED+280; and CD=EDC−266, and displays these values in their appropriate fields at step 91. The 50-percentile value of EFW in grams and pounds/ounces is also updated and displayed at step 92 by executing the same steps described above for step 69. The system then returns to step 81 so that the "EDC" field will continue to blink the EDC value, allowing the user to continue scrolling until the desired EDC value appears on the field. The user then must press the "enter" button 11 to accept the displayed EDC at step 83.

Figure 11:
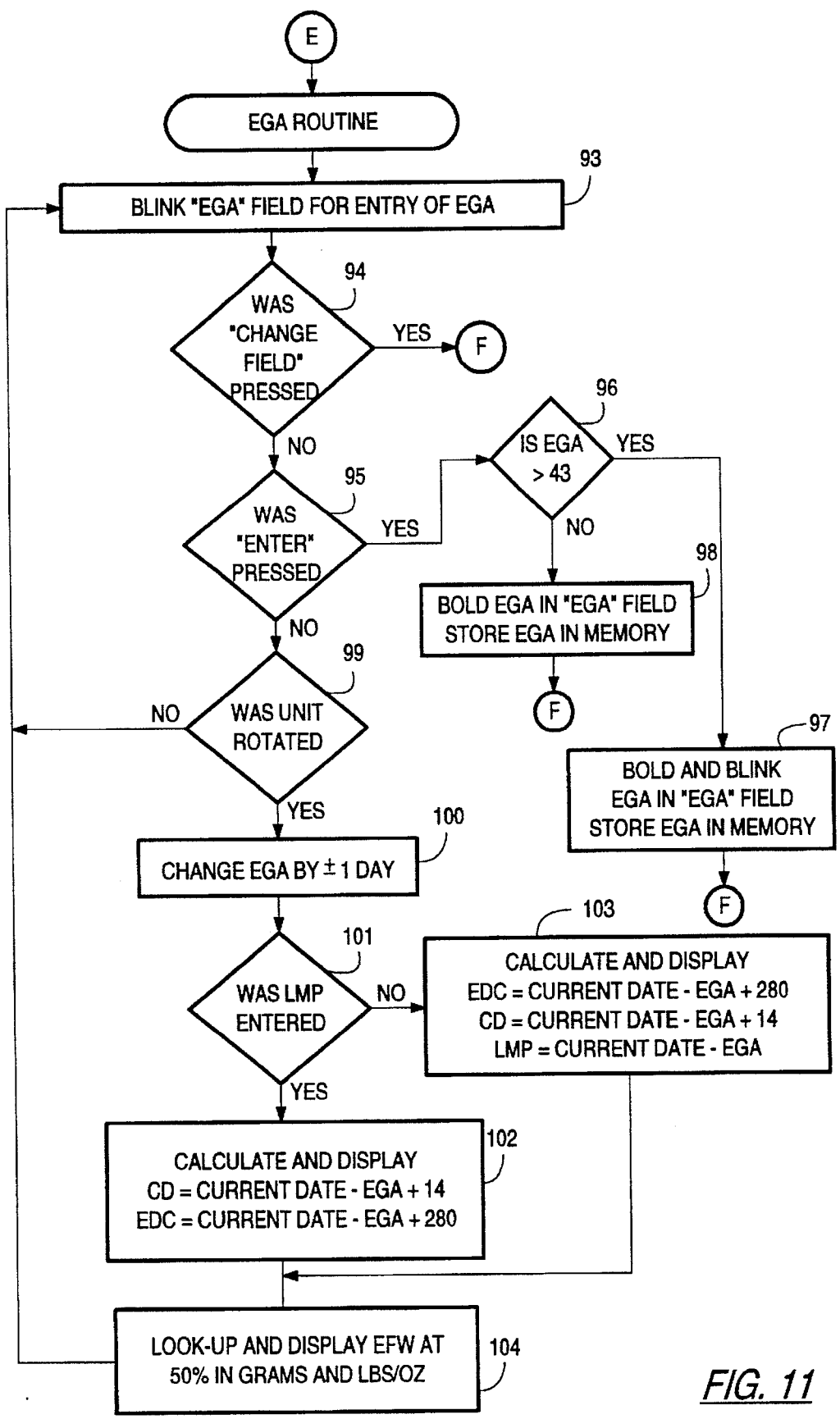

Once the EDC value has been entered, the system advances to the EGA routine of step 58 in FIG. 7. FIG. 11 is a flow chart of the EGA routine. At step 93, the "EGA" field containing the default EGA is blinked to prompt the user to enter a EGA value. If the user does not wish to enter in a EGA value, the "change field" button 12 may be pressed to produce an affirmative answer at step 94. This causes the system to bypass the EGA routine and jump directly to the CD routine in FIG. 12.

Step 95 determines whether the user has pressed the "enter" button 11 to accept the displayed EGA. An affirmative answer at this step advances the system to step 96 which tests the entered EGA value. If the EGA value entered is greater than forty-three weeks, the user has entered erroneous data. An affirmative answer at step 96 stores the EGA in memory and bolds and blinks the EGA value in the "EGA" field at step 97 to indicate an erroneous EGA was entered. A negative response at step 96 stores the EGA in memory and bolds the EGA value in the "EGA" field at step 98 to indicate an appropriate EGA was entered.

A negative answer at step 95 advances the system to step 99 which determines whether the user has turned the annulus 13 to initiate scrolling of the displayed EGA. An affirmative answer at step 99 changes the displayed EGA by one day at step 100. A negative response at step 99 returns the system to step 93.

Each time the EGA is changed by the user, the microprocessor updates the other gestational values. First, step 101 tests whether a LMP value was previously entered by the user. An affirmative answer at step 101 updates the CD and EDC gestational values by calculating EDC=(current date) −EGA+280; and CD=(current date)−EGA+14, and displays these values in their appropriate fields at step 102. A negative response at step 101 updates the LMP, CD and EDC gestational values by calculating LMP=(current date) −EGA; EDC=(current date)−EGA+280; and CD=(current date)−EGA+14, and displays these values in their appropriate fields at step 103. The 50-percentile value of EFW in grams and pounds/ounces is also updated and displayed at step 104 by executing the same steps described above for step 69. The system then returns to step 93 so that the "EGA" field will continue to blink the EGA value, allowing the user to continue scrolling until the correct EGA value appears on the field. The user then must press the "enter" button 11 to accept the displayed EGA at step 95.

Figure 12:
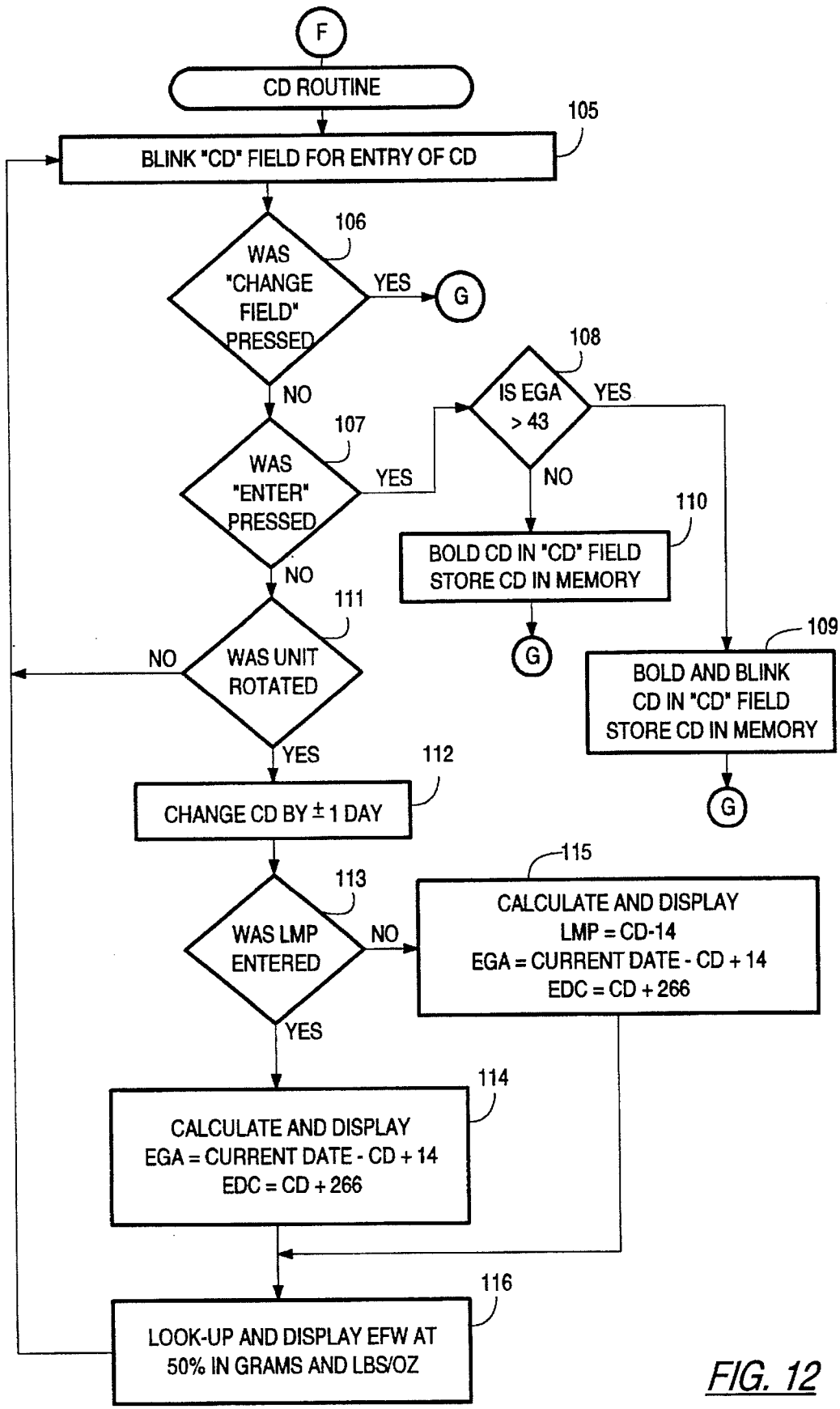

Once the EGA value has been entered, the system advances to the CD routine of step 59 in FIG. 7. FIG. 12 is a flow chart of the CD routine. At step 105, the "CD" field containing the default CD is blinked to prompt the user to enter a CD value. If the user does not wish to enter in a CD value, the "change field" button 12 may be pressed to produce an affirmative answer at step 106. This causes the system to bypass the CD routine and jump directly to the U/S Date routine in FIG. 13.

Step 107 determines whether the user has pressed the "enter" button 11 to accept the displayed CD. An affirmative answer at this step advances the system to step 108 which tests the entered CD value. If the EGA value calculated from the entered CD is greater than forty-three weeks, the user has entered erroneous data. An affirmative answer at step 108 stores the CD in memory and bolds and blinks the CD value in the "CD" field at step 109 to indicate an erroneous CD was entered. A negative response at step 108 stores the CD in memory and bolds the CD value in the "CD" field at step 110 to indicate an appropriate LMP was entered.

A negative answer at step 107 advances the system to step 111 which determines whether the user has turned the annulus 13 to initiate scrolling of the displayed CD. An affirmative answer at step 111 changes the displayed CD by one day at step 112. A negative response at step 111 returns the system to step 105.

Each time the CD is changed by the user, the microprocessor updates the other gestational values. First, step 113 tests whether a LMP value was previously entered by the user. An affirmative answer at step 113 updates the EDC and EGA gestational values by calculating EGA=(current date) −CD+14; EDC=CD+266, and displays these values in their appropriate fields at step 114. A negative response at step 113 updates the LMP, CD and EDC gestational values by calculating LMP=CD−14, EGA=(current date)−CD+14; EDC=CD+266, and displays these values in their appropriate fields at step 115. The 50-percentile value of EFW in grams and pounds/ounces is also updated and displayed at step 116 by executing the same steps described above for step 69. The system then returns to step 105 so that the "CD" field will continue to blink the CD value, allowing the user to continue scrolling until the desired CD value appears on the field. The user then must press the "enter" button 11 to accept the displayed CD at step 107.

Figure 13:
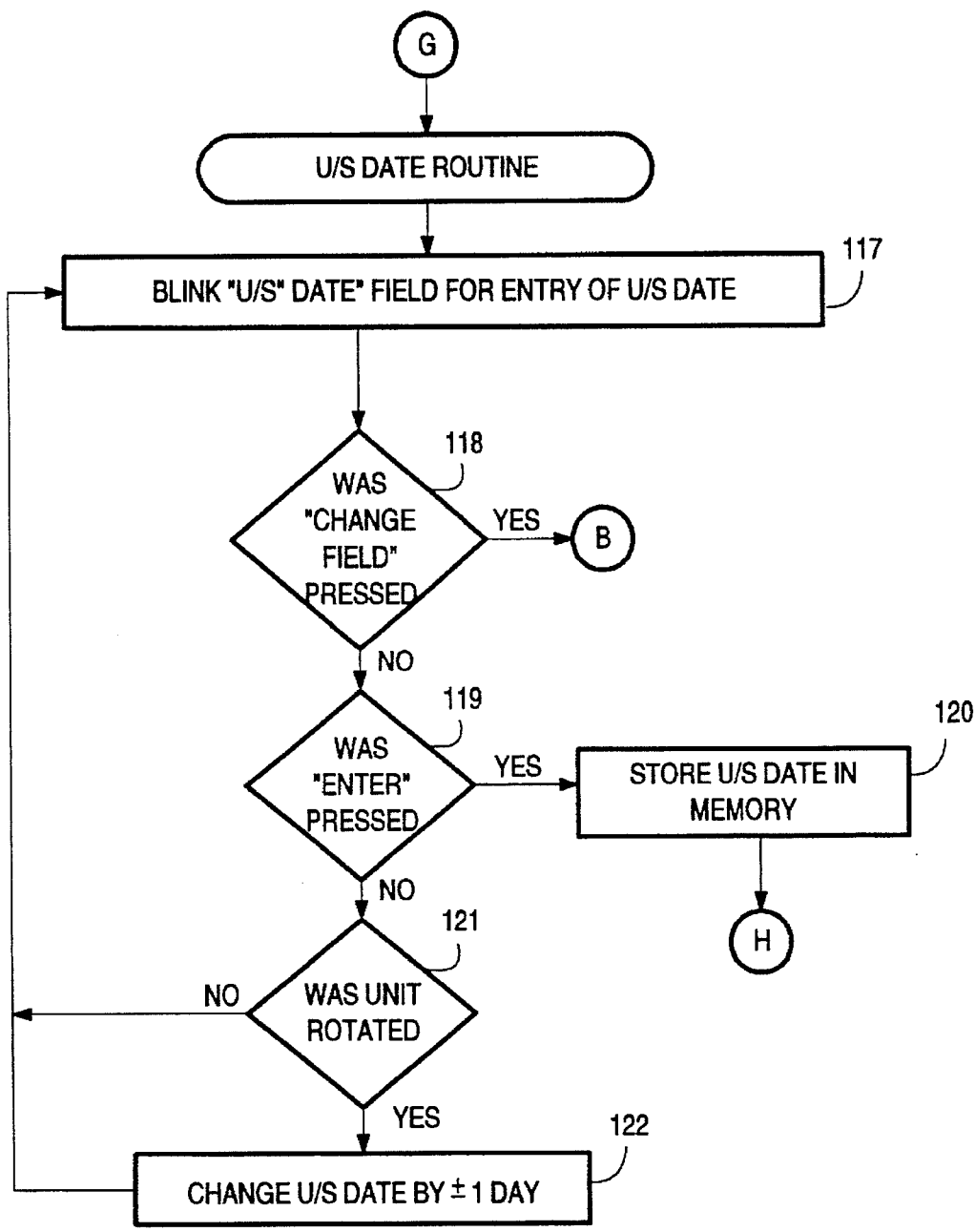

After the CD value has been entered, the system advances to the U/S Date routine of step 60 in FIG. 7. FIG. 13 is a flow chart of the U/S Date routine. At step 117, the "U/S Date" field containing the current date is blinked to prompt the user to enter the correct U/S Date. If the user does not wish to enter in a U/S Date, the "change field" button 12 may be pressed to produce an affirmative answer at step 118. This causes the system to bypass the U/S Date routine and jump back to the default gestational values routine in FIG. 8.

Step 119 determines whether the user has pressed the "enter" button 11 to accept the displayed U/S Date as the correct U/S Date; an affirmative answer at this step stores the U/S Date in memory at step 120. A negative answer at step 119 advances the system to step 121 which determines whether the user has turned the annulus 13 to initiate scrolling of the displayed U/S Date. A negative response at step 121 returns the system to step 117. An affirmative answer at step 121 changes the displayed U/S Date by one day at step 122. The system then returns to step 117 so that the "U/S Date" field will continue to blink the U/S Date value, allowing the user to continue scrolling until the correct U/S Date value appears on the field. The user then must press the "enter" button 11 to accept the displayed U/S Date at step 119.

Figure 14A:
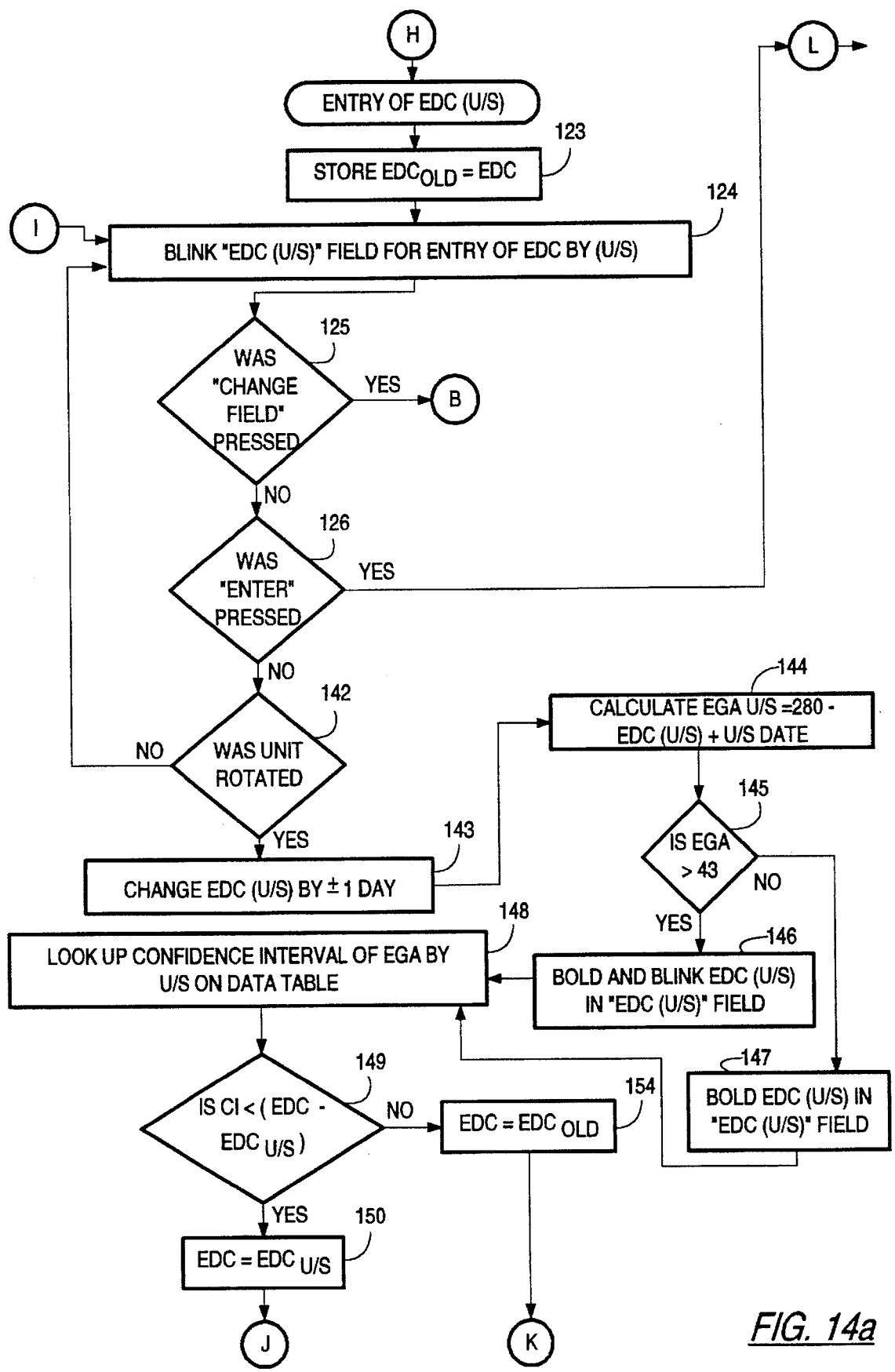
Figure 14B:
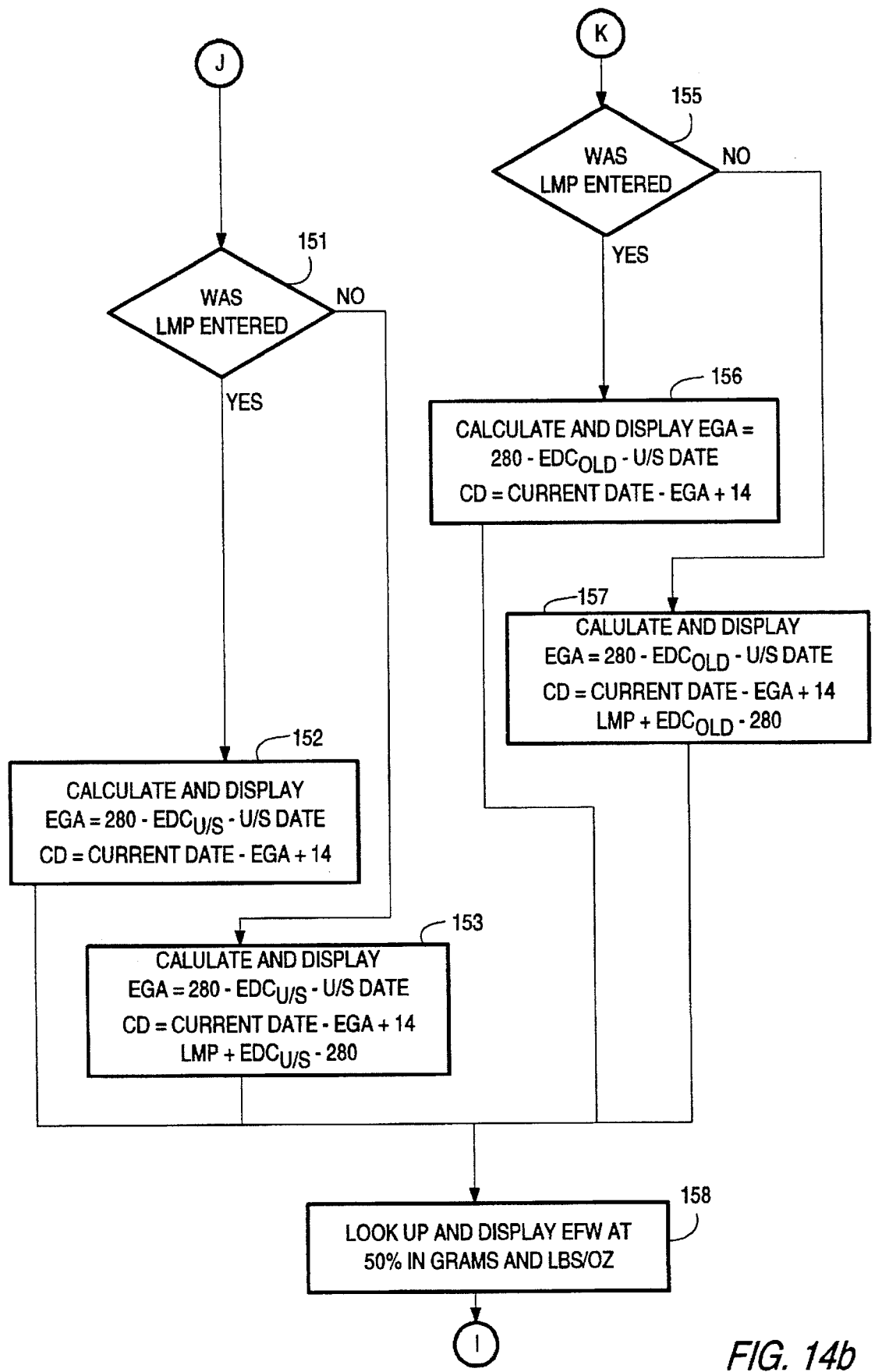
Figure 14C:
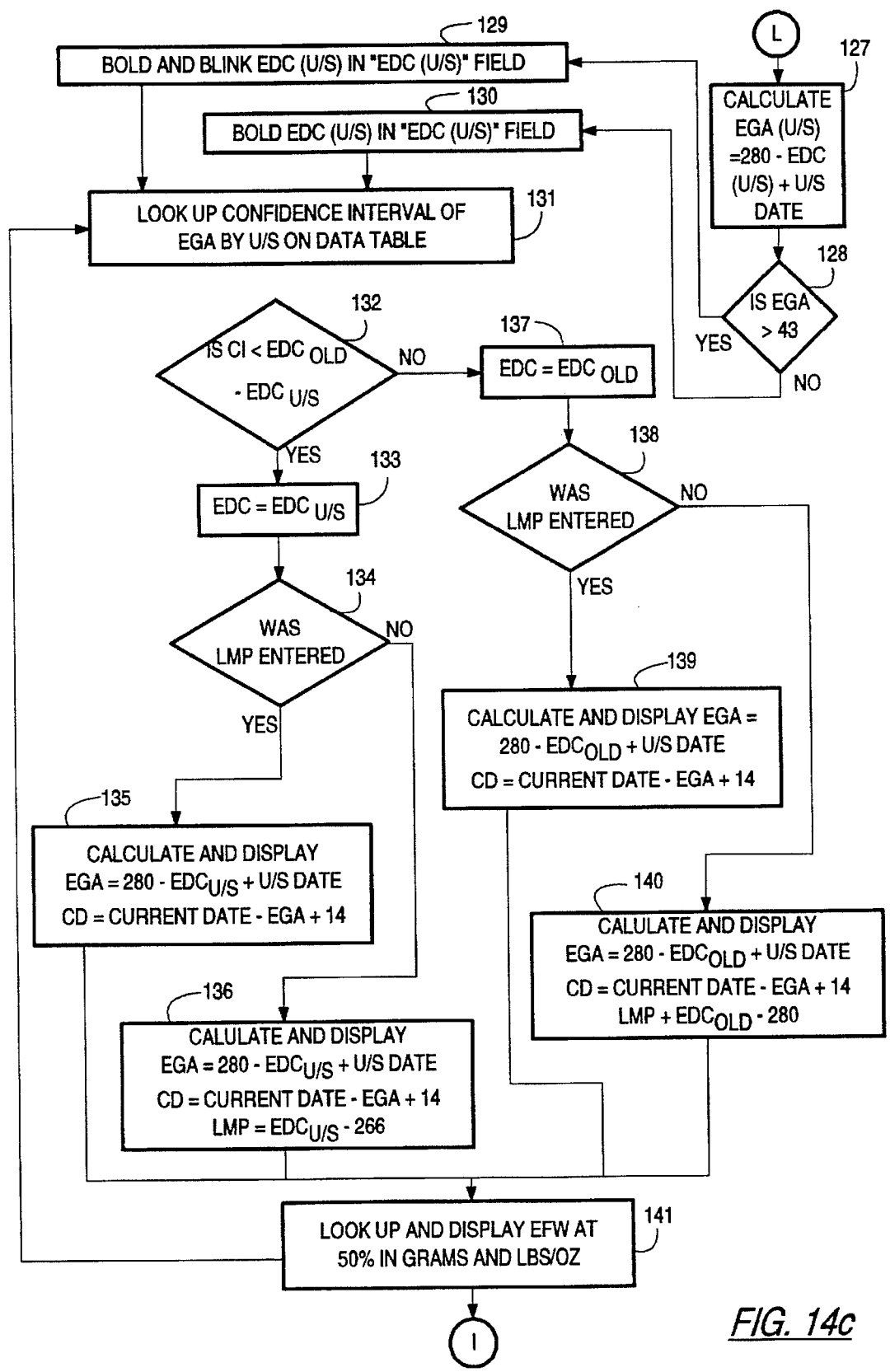

After the U/S Date has been entered, the system advances to the EDC (U/S) routine of step 64 in FIG. 7. FIG. 14 shows a flow chart of the EDC (U/S) routine. At step 123, the last calculated value of EDC is stored as $EDC_{old}$. At step 124, the "EDC (U/S)" field containing a default value is blinked to prompt the user to enter a EDC (U/S) value. If the user does not wish to enter in a EDC (U/S) value, the "change field" button 12 may be pressed to produce an affirmative answer at step 125. This causes the system to bypass the EDC (U/S) routine and jump back to the default gestational values murine in FIG. 8.

Step 126 determines whether the user has pressed the "enter" button 11 to accept the displayed EDC (U/S). An affirmative answer at this step instructs the microprocessor to test for the most accurate gestational values.

To calculate the most accurate gestational values, step 127 calculates the $EGA_{U/S}$ with the equation $EGA_{U/S}=280-EDC_{U/S}+$(U/S Date). Next, step 128 tests whether the EGA value calculated from the entered EDC (U/S) is greater than forty-three weeks; if so, the user has entered erroneous data. An affirmative answer at step 128 bolds and blinks the EDC (U/S) in the "EDC (U/S)" field at step 129 to indicate an erroneous EDC (U/S) was entered. A negative answer at step 128 bolds the EDC (U/S) in the "EDC (U/S)" field at step 130 to indicate an appropriate EDC (U/S) was entered.

Step 131 uses this calculated $EGA_{U/S}$ value to obtain the confidence interval of $EGA_{U/S}$ from the data in Table 2. Next at step 132, the confidence interval is tested to determine if it is less than or equal to the absolute value of the difference between $EDC_{old}$ and $EDC_{U/S}$.

If step 132 is answered in the affirmative, $EDC_{U/S}$ is the most accurate EDC value to calculate the other gestational parameters at step 133. Next, step 134 tests whether a LMP value was previously entered by the user. An affirmative answer at step 134 updates the EGA and CD gestational values by calculating EGA=28031 $EDC_{U/S}$+(U/S Date); and CD=$EDC_{U/S}$–266, and displays these values in their appropriate fields at step 135. A negative answer at step 134 updates the LMP, EGA and CD gestational values by calculating LMP=$EDC_{U/S}$–266, EGA=(U/S Date)–$EDC_{U/S}$–280; CD=$EDC_{U/S}$–266, and displays these values in their appropriate fields at step 136.

If step 132 is a negative response, $EDC_{old}$ is the most accurate EDC value to calculate the other gestational parameters at step 137. Next, step 138 tests whether a LMP value was previously entered by the user. An affirmative answer at step 138 updates the EGA and CD gestational values by calculating EGA=280–$EDC_{old}$+(U/S Date); and CD=$EDC_{old}$–266, and displays these values in their appropriate fields at step 139. A negative answer at step 138 updates the LMP, EGA and CD gestational values by calculating LMP=$EDC_{old}$–266, EGA=(U/S Date)–$EDC_{old}$+280; CD=$EDC_{old}$–266, and displays these values in their appropriate fields at step 140. The 50-percentile value of EFW in grams and pounds/ounces is also updated and displayed at step 141 by executing the same steps described above for step 69. After the most accurate gestational values have been calculated and displayed, the system advances to the changing EFW routine in FIG. 15.

A negative answer at step 126 advances the system to step 142 which determines whether the user has turned the annulus 13 to initiate scrolling of the displayed EDC (U/S). An affirmative answer at step 142 changes the displayed EDC (U/S) by one day at step 143. A negative response at step 142 returns the system to step 124. Each time the EDC (U/S) is changed by the user, the most accurate gestational values are update. The process of steps 144 to 158 is identical to that just explained above. The system then returns to step 124 so that the EDC (U/S) will continue to blink the EDC (U/S) value, allowing the user to continue scrolling until the desired EDC (U/S) value appears on the field. The user must then press the "enter" button 11 to accept the displayed EDC (U/S) at step 126.

Figure 15B:
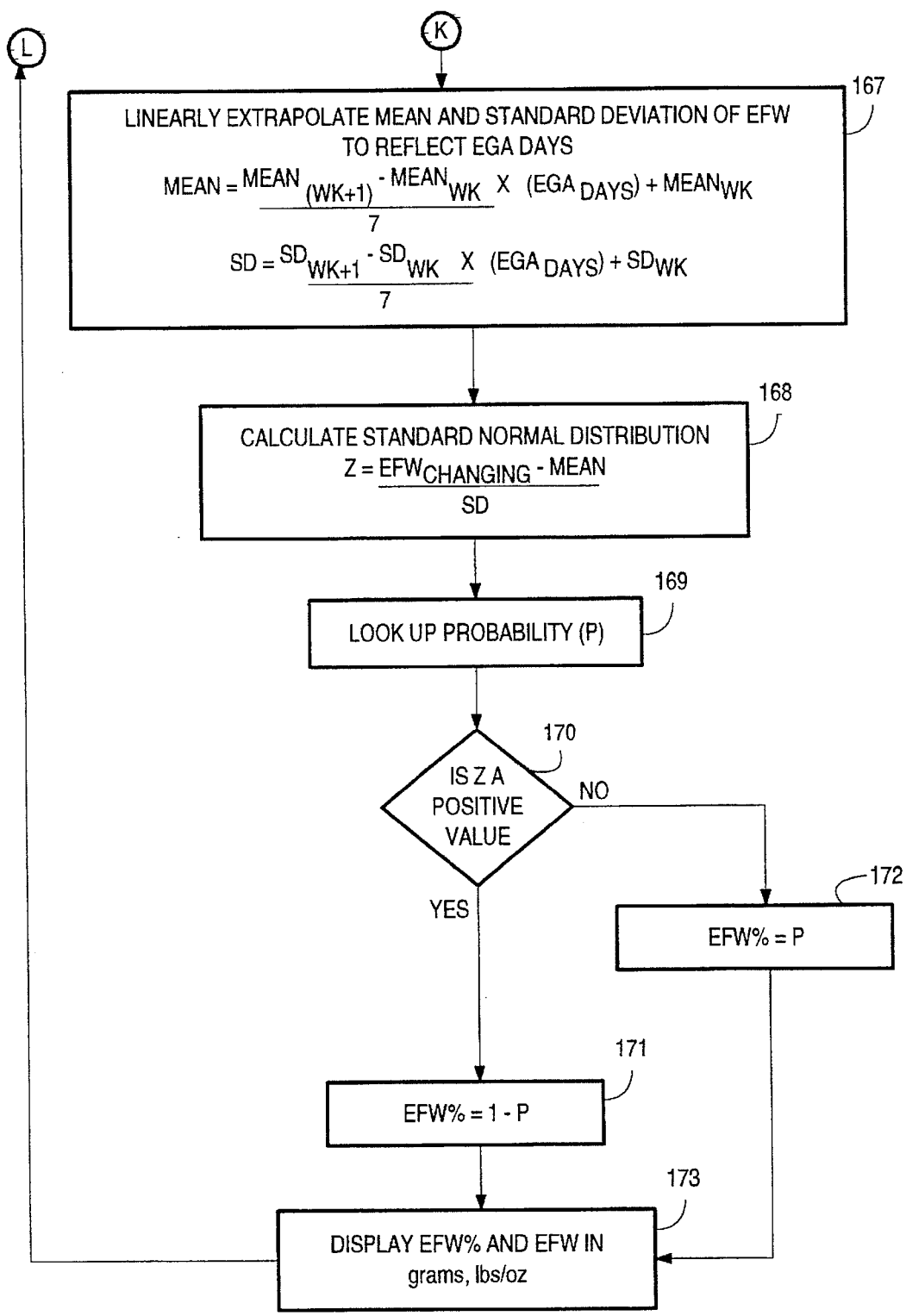
Figure 15A:
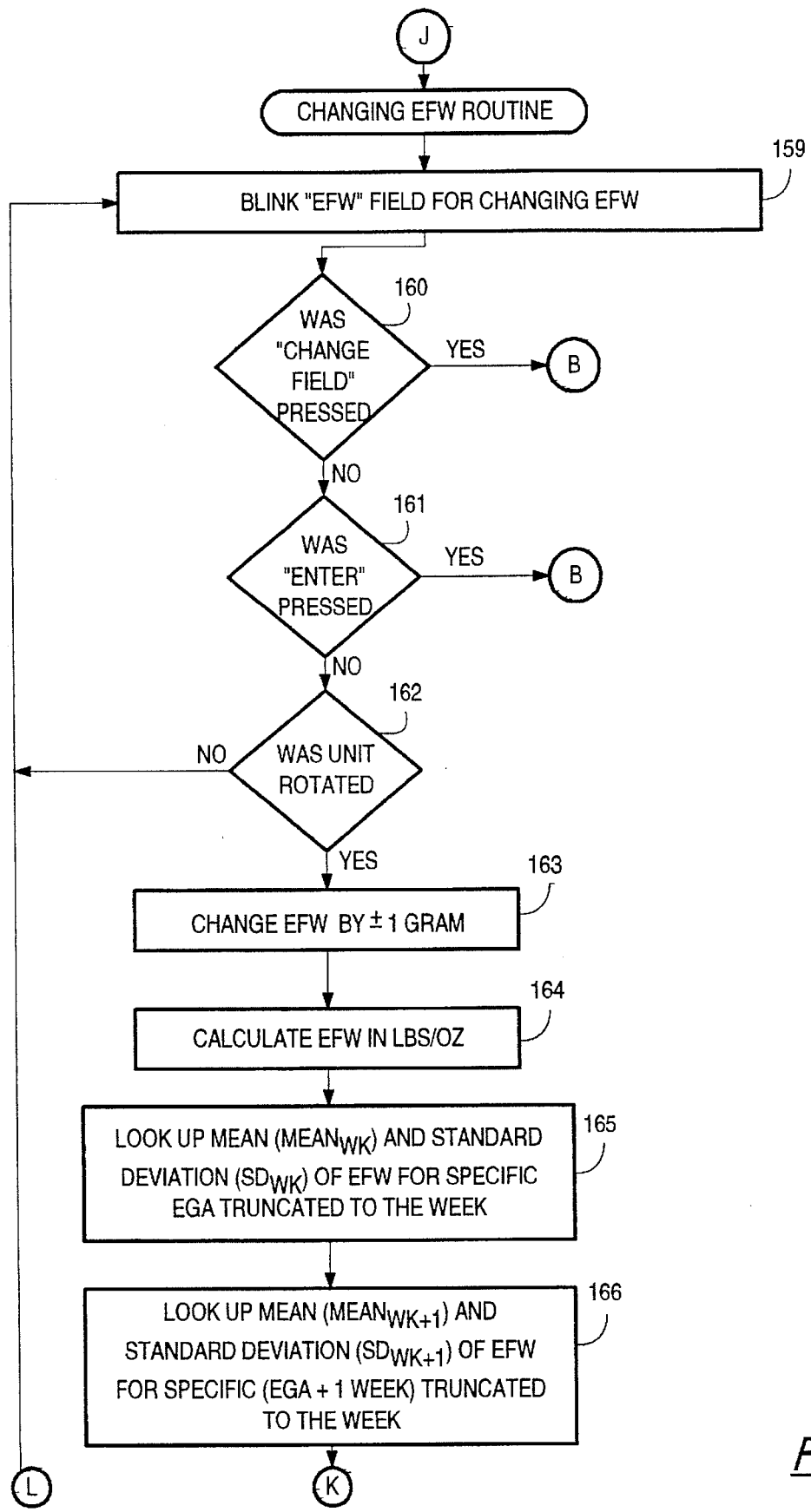

After the EDC (U/S) has been entered and the most accurate gestational values displayed, the system advances to the changing EFW routine of step 66 in FIG. 7. FIG. 15 shows a flow chart of the changing EFW routine. At step 159, the "EFW" field containing the most accurate EFW in grams at 50% is blinked to prompt the user to change the EFW in grams and obtain the corresponding percentile. If the user does not wish to change the EFW, the "change field" button 12 may be pressed to produce an affirmative answer at step 160. This causes the system to bypass the changing EFW routine and jump back to the default gestational values routine in FIG. 8.

Step 161 determines whether the user has pressed the "enter" button 11 to stop changing the EFW, and an affirmative answer at this step jumps the system back to the default gestational values routine in FIG. 8. A negative answer at step 145 advances the system to step 162 which determines whether the user has turned the annulus 13 to initiate scrolling the displayed EFW in grams. A negative response at step 162 returns the system to step 159. An affirmative answer at step 162 changes the displayed EFW by one gram at step 163. Each time the EFW is changed by the user, the microprocessor updates the EFW in pounds/ounces at step 164.

Next, the corresponding EFW percentile for the updated EFW in grams is calculated and displayed. Step 165 obtains the mean and standard deviation of the EFW for the specific EGA from Table 3. The EGA value is in terms of weeks and days while Table 3 only contains EGA values in terms of weeks, so the EGA value is truncated to weeks to use Table 3. At step 166, the mean and standard deviation of the specific EGA plus one week is obtained from Table 3. The mean and standard deviation values are linearly extrapolated at step 167 to reflect the days portion of the EGA. The extrapolated mean and standard deviation (SD) are calculated with the equations mean=$(mean_{wk+1}-mean_{wk})*(EGA_{days})/7+mean_{wk}$, and SD=$(SD_{wk+1}-SD_{wk})*(EGA_{days})/7+SD_{wk}$. Step 168 calculates the standard normal distribution (z) of the changing EFW value with the equation z=$(EFW_{changing}-mean)/SD$. The absolute value of the calculated standard normal distribution is used to obtain a probability value from Table 4 at step 169. Step 170 tests whether the standard normal distribution is a positive value. An affirmative answer at step 170 calculates the EFW percentile as one minus the probability value at step 171. A negative answer at step 170 calculates the EFW percentile as the probability value at step 172.

The EFW in grams and pounds/ounces and its percentile are displayed in the "EFW" field at step 173. The system then returns to step 159 so that the "EFW" field will continue to blink the EFW, allowing the user to continue scrolling until the desired EFW in grams, pounds/ounces and percentile have been displayed. The user must then press the "enter" button 11 or "change field" button 12 to restart the main program jumping to the default gestational values routine in FIG. 8.

The gestational computer described above can be modified in various ways to fit the specific needs of different users. For example, several additional fields may be added to satisfy the medical user. For example, the gestational computer could display derived averages for ultrasonic data of any given fetal age to help determine normal ranges. Another display field could guide the proper timing of specialized testing such as MSAFP, CVS, amniocentesis, diabetic, and other blood work. A display field could also be added to describe the fetus' organ formation and function for the calculated ages.

Additional fields may also be added to the gestational computer to fit the needs of patients. For example, the computer display could inform the user of developmental features of the fetus during the calculated ages and of other fetal achievements such as first movements, sucking thumb and opening eyes. Another field could inform the user of possible risk factors at certain times throughout the pregnancy. The gestational computer could also be programmed to hold specific information for the owner such as name, medical emergency information and medications.

The gestational computer can be programmed for any gestational cycle of any organism. Veterinarians and biological researchers could quickly obtain the gestational calculations from this hand held unit. The main program described above could be modified such that the calculations performed would match the gestational cycle of the target organism.

TABLE 1

| EGA (weeks) | EFW (grams) |
|---|---|
| <21 | 0 |
| 21 | 460 |
| 22 | 460 |
| 23 | 630 |
| 24 | 630 |
| 25 | 820 |
| 26 | 820 |
| 27 | 1000 |
| 28 | 1000 |
| 29 | 1300 |
| 30 | 1300 |
| 31 | 1700 |
| 32 | 1700 |
| 33 | 2100 |
| 34 | 2100 |
| 35 | 2500 |
| 36 | 2500 |
| 37 | 2900 |
| 38 | 2900 |
| 39 | 3400 |
| 40 | 3400 |
| 41 | 3400 |

TABLE 2

| $EGA_{U/S}$ (weeks) | Confidence Interval of $EGA_{U/S}$ (days) |
|---|---|
| <5 | 270 |
| >= 5 and < 6 | 9 |
| >= 6 and < 12 | 5 |
| >= 12 and < 20 | 10 |
| >= 20 and < 26 | 14 |
| >= 26 and < 30 | 21 |
| >= 30 and < 42 | 28 |
| >= 42 | 270 |

TABLE 3

| EGA (weeks) | EFW Mean (grams) | EFW Standard Deviation (grams) |
|---|---|---|
| 21 | 472 | 27 |
| 22 | 562 | 30 |
| 23 | 663 | 34 |
| 24 | 773 | 38 |
| 25 | 895 | 43 |
| 26 | 1026 | 47 |
| 27 | 1169 | 53 |
| 28 | 1321 | 60 |
| 29 | 1483 | 66 |
| 30 | 1655 | 75 |
| 31 | 1837 | 85 |
| 32 | 2027 | 95 |
| 33 | 2225 | 106 |
| 34 | 2431 | 120 |
| 35 | 2644 | 133 |
| 36 | 2864 | 150 |
| 37 | 3088 | 169 |
| 38 | 3318 | 189 |
| 39 | 3552 | 211 |
| 40 | 3788 | 236 |
| 41 | 4027 | 262 |
| 42 | 4268 | 291 |

TABLE 4

| z | P | z | P |
|---|---|---|---|
| 0.0 | 0.50 | 0.6745 | 0.25 |
| 0.0251 | 0.49 | 0.7063 | 0.24 |
| 0.0502 | 0.48 | 0.7388 | 0.23 |
| 0.0753 | 0.47 | 0.7722 | 0.22 |
| 0.1004 | 0.46 | 0.8064 | 0.21 |
| 0.1257 | 0.45 | 0.8416 | 0.20 |
| 0.1510 | 0.44 | 0.8779 | 0.19 |
| 0.1764 | 0.43 | 0.9154 | 0.18 |
| 0.2019 | 0.42 | 0.9542 | 0.17 |
| 0.2275 | 0.41 | 0.9945 | 0.16 |
| 0.2533 | 0.40 | 1.036 | 0.15 |
| 0.2793 | 0.39 | 1.080 | 0.14 |
| 0.3055 | 0.38 | 1.1264 | 0.13 |
| 0.3319 | 0.37 | 1.175 | 0.12 |
| 0.3585 | 0.36 | 1.227 | 0.11 |
| 0.3853 | 0.35 | 1.282 | 0.10 |
| 0.4125 | 0.34 | 1.341 | 0.09 |
| 0.4399 | 0.33 | 1.405 | 0.08 |
| 0.4677 | 0.32 | 1.476 | 0.07 |
| 0.4959 | 0.31 | 1.555 | 0.06 |
| 0.5244 | 0.30 | 1.645 | 0.05 |
| 0.5534 | 0.29 | 1.751 | 0.04 |
| 0.5828 | 0.28 | 1.881 | 0.03 |
| 0.6128 | 0.27 | 2.054 | 0.02 |
| 0.6433 | 0.26 | 2.326 | 0.01 |

We claim:
1. A hand-held gestational computer comprising
    a microprocessor programmed to receive input signals representing the current date and at least one parameter selected from the group consisting of the date of the first day of the last menstrual period, estimated gestation age, conception date, estimated date of confinement by ultrasound analysis, and estimated fetal weight, and to produce output signals representing the value of at least one parameter selected from the group consisting of estimated gestation age, estimated date of confinement, conception date, estimated fetal weight, and the percentile of the estimated fetal weight for the estimated gestation age, display means responsive to said output signals for producing displays of the parameter values represented by said output signals, a palm-sized housing for said microprocessor and said display means, first manually operable means connected to said microprocessor for sequentially selecting different display fields in which data is to be entered, and second manually operable means connected to said microprocessor for sequentially displaying data available for entry in the display field selected by said first manually operable means.

2. The gestational computer of claim 1 which includes third manually operable means connected to said microprocessor for entering selected data in a selected display field.

3. The gestational computer of claim 1 wherein said palm-sized housing is generally circular in shape, and said second manually operable means includes an annular actuator mounted for rotational movement on said housing.

4. The gestational computer of claim 3 which includes signal generating means responsive to the rotational position of said annular actuator for supplying said microprocessor with control signals representing the direction and rate of change of the sequentially displayed data.

5. A hand-held gestational microprocessor comprising a microprocessor programmed to receive input signals representing the current date and at least one parameter selected from the group consisting of the date of the first day of the last menstrual period, estimated gestation age, conception date, estimated date of confinement by ultrasound analysis, and estimated fetal weight, and producing output signals representing the value of at least one parameter selected from the group consisting of estimated gestation age, estimated date of confinement, conception date, estimated fetal weight, and the percentile of the estimated fetal weight for the estimated gestation age, display means responsive to said output signals for producing displays of the parameter values represented by said output signals, and a memory connected to said microprocessor for storing data representing a fetal weight for each of a range of different gestation ages, said microprocessor being programmed to retrieve and display the fetal weight corresponding to the displayed estimated gestation age.

6. The gestational microprocessor of claim 3 wherein said fetal weight is the 50-percentile fetal weight.

7. A hand-held gestational microprocessor comprising a microprocessor programmed to receive input signals representing the current date and at least one parameter selected from the group consisting of the date of the first day of the last menstrual period, estimated gestation age, conception date, estimated date of confinement by ultrasound analysis, and estimated fetal weight, and producing output signals representing the value of at least one parameter selected from the group consisting of estimated gestation age, estimated date of confinement, conception date, estimated fetal weight, and the percentile of the estimated fetal weight for the estimated gestation age, display means responsive to said output signals for producing displays of the parameter values represented by said output signals, a memory connected to said microprocessor for storing data indicating whether the computed estimated gestation age, or the gestation age estimated from ultrasound analysis, is preferred for each of a range of combinations of values of the two estimated ages, and said microprocessor being programmed to retrieve and display the estimated gestation age preferred for the current values of the two estimated ages.

8. The gestational microprocessor of claim 5 wherein said display means includes separate displays of the computed estimated gestation age and the gestation age estimated from ultrasound analysis.

9. The gestational microprocessor of claim 5 wherein said display means includes a separate display of the date of the ultrasound analysis.

10. A hand-held gestational microprocessor comprising a microprocessor programmed to receive input signals representing the current date and at least one parameter selected from the group consisting of the date of the first day of the last menstrual period, estimated gestation age, conception date, estimated date of confinement by ultrasound analysis, and estimated fetal weight, and producing output signals representing the value of at least one parameter selected from the group consisting of estimated gestation age, estimated date of confinement, conception date, estimated fetal weight, and the percentile of the estimated fetal weight for the estimated gestation age, display means responsive to said output signals for producing displays of the parameter values represented by said output signals, a memory connected to said microprocessor for storing data representing the percentile number for each of a range of different combinations of fetal weight and gestation age, and said microprocessor being programmed to retrieve and display the percentile number corresponding to the displayed estimated fetal weight and estimated gestation age.

* * * * *